United States Patent [19]

Isshiki et al.

[11] Patent Number: 4,828,762
[45] Date of Patent: May 9, 1989

[54] PROCESS FOR THE PRODUCTION OF 2,3,5-TRIMETHYLBENZOQUINONE

[75] Inventors: Tomiya Isshiki, Tokyo; Tomoyuki Yui, Matsudo; Mitsuo Abe, Tokyo; Masahiro Jono, Tokyo; Hideo Uno, Tokyo, all of Japan

[73] Assignee: Mitsubishi Gas Chemical Company, Inc., Tokyo, Japan

[21] Appl. No.: 947,503

[22] Filed: Dec. 29, 1986

Related U.S. Application Data

[63] Continuation-in-part of Ser. No. 749,191, Jun. 26, 1985, abandoned, and a continuation-in-part of Ser. No. 796,485, Nov. 6, 1985, abandoned, which is a continuation-in-part of Ser. No. 615,125, May 30, 1984, abandoned.

[30] Foreign Application Priority Data

Jun. 6, 1983 [JP] Japan ................. 58-100624
Jul. 3, 1984 [JP] Japan ................. 59-137710

[51] Int. Cl.⁴ .......................................... C07C 50/04
[52] U.S. Cl. ........................................... 260/396 R
[58] Field of Search ................................. 260/396 R

[56] References Cited

U.S. PATENT DOCUMENTS

| | | | |
|---|---|---|---|
| 3,391,053 | 7/1968 | Kolh .................. | 161/185 |
| 3,574,030 | 7/1968 | Callander et al. ...... | 156/244 |
| 3,625,983 | 12/1971 | Wollensak ............ | 260/396 |
| 3,796,732 | 3/1974 | Brenner .............. | 260/396 |
| 4,208,339 | 6/1980 | Costantini et al. .... | 260/396 |
| 4,442,036 | 4/1984 | Hsu et al. ........... | 260/396 R |
| 4,491,545 | 1/1985 | Thoemel et al. ....... | 260/396 |

FOREIGN PATENT DOCUMENTS

| | | | |
|---|---|---|---|
| 0070665 | 1/1983 | European Pat. Off. ...... | 260/396 R |
| 0084448 | 7/1983 | European Pat. Off. ...... | 260/396 |
| 0107427 | 5/1984 | European Pat. Off. ...... | 260/396 R |
| 0127888 | 12/1984 | European Pat. Off. ...... | 260/396 R |
| 3215095 | 10/1983 | Fed. Rep. of Germany .... | 260/396 |

OTHER PUBLICATIONS

*Mellor's Comprehensive Treatise on Inorganic and Theoretical Chemistry*, vol. III, supplement III.

Primary Examiner—Glennon H. Hollrah
Assistant Examiner—Raymond Covington
Attorney, Agent, or Firm—Frishauf, Holtz, Goodman & Goodman

[57] ABSTRACT

A process for the production of 2,3,5-trimethylbenzoquinone (TMBQ) from 2,3,6-trimethylphenol (TMP) is described, comprising contacting TMP with oxygen or an oxygen containing gas in a medium of water and an aliphatic alcohol having from 5 to 10 carbon atoms in the presence of catalyst of a copper halogen complex represented by the formula as shown below or a mixture of the copper halogen complex and an alkali metal halide or a mixture of the copper halogen complex, an alkali metal halide and cupric hydroxide and/or cuprous chloride

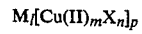

$$M_l[Cu(II)_m X_n]_p$$

wherein M is an alkali metal or ammonium, Cu(II) is a divalent copper, X is a halogen atom, l is an integer of 1 to 3, m is 1 or 2, n is an integer or 3 to 8, p is 1 or 2, and 1+2mp=np. The process is carried out in a batch system, a semi-batch system or in a continuous flow system. The third mentioned catalyst system is most effectively utilized in the semi-batch system. The present process yields various advantages; for example, TMBQ can be produced with high selectivity, and since the reaction is performed in a specific medium (the medium is heterogeneous because the alcohols are immiscible or only slightly miscible with water) and TMBQ is soluble in the alcohol layer, while the catalyst is soluble in the water layer, the TMBQ can be easily separated and reuse of the catalyst can be accomplished by a simplified procedure. TMBQ is a useful compound as an intermediate for use in the preparation of Vitamin E.

30 Claims, No Drawings

PROCESS FOR THE PRODUCTION OF 2,3,5-TRIMETHYLBENZOQUINONE

This application is a continuation-in-part (i) of application Ser. No. 749,191, filed June 26, 1985, now abandoned, and (ii) of application Ser. No. 796,485 filed Nov. 6, 1985, now abandoned, which in turn is a continuation in part of application Ser. No. 615,125 filed May 30, 1984, now abandoned.

The present invention relates to a process for the preparation of 2,3,5-trimethylbenzoquinone (hereinafter "TMBQ"). More particularly, it is concerned with a process for preparing TMBQ by oxidizing 2,3,6-trimethylphenol (hereinafter "TMP") with oxygen in an aliphatic alcohol having from 5 to 10 carbon atoms in the presence of an aqueous catalyst solution comprising a copper halogeno complex, a copper halogeno complex and an alkali metal halide or a copper halogeno complex, an alkali metal halide and cupric hydroxide and/or cuprous chloride.

TMBQ is a useful substance as an intermediate for use in the preparation of Vitamin E.

It is known that TMBQ can be prepared from various starting materials. The present invention is concerned with a process for the production of TMBQ from TMP as a starting material.

Typical known methods for the production of TMBQ from TMP include the following:

(1) the oxidation of TMP with an inorganic oxidizing agent; and (2) the oxidation of TMP with oxygen in the presence of a catalyst.

Inorganic oxidizing agents as used in method (1) include potassium permanganate, manganese dioxide, and lead oxide. Method (1), however, has disadvantages associated with it in that it required stoichiometric amounts of the expensive oxidizing agents and it is necessary to treat or regenerate the metals in a reduced valency state which result from the oxidation reaction.

As the catalyst for use in method (2), a cobalt complex catalyst, for example, is known (Japanese Patent Publication No. 2446/1974). This method, however, is not suitable for industrial use since the life of the catalyst is very short although its activity is quite high at the initial stage of the reaction. In addition, a method has been proposed in which copper halide is used as the catalyst. This method is characterized by both high yields and selectivity under limited conditions, however there still remains certain fundamental problems to be solved for the industrial practice of the method.

Japanese Patent Publication No. 17585/1978, discloses a method of oxidizing TMP with oxygen using a catalyst of copper and halogen ions. Although these methods are superior in that the yields are high under limited conditions, they are associated with the disadvantages that the rate of reaction is low, the influence of water on the reaction very serious, and in that a large amount of energy is required for the isolation of TMBQ and/or reuse of the catalyst. When the catalyst is intended to be recovered and reused after the reaction is completed, it is necessary that the reaction solution be extracted with a large quantity of water, the resulting aqueous solution is freed of water by techniques such as evaporation, and the catalyst be recovered in a water-free condition. In industrially recovering and reusing the catalyst, a large amount of energy is consumed, which is a serious disadvantage from an economic standpoint. Furthermore, since the catalyst is of low activity, the method has the disadvantage that the reaction time is long, the space time yield low, and the reactor is required to be increased in size.

Using the method of Japanese Patent Publication No. 17585/1978, satisfactory results can be obtained only when the reaction is carried out using a copper chloride catalyst and a dimethylformamide or ethylene glycol solvent. Thus, when a copper bromide catalyst, for example, is used, or the reaction is carried out with a copper chloride catalyst in acetone containing water, the yield and selectivity of TMBQ are not satisfactory. This means that in the case of the catalyst comprising copper and halogen ions, satisfactory results can be obtained only when the reaction system does not contain water and copper chloride is used as the catalyst. When copper chloride is used as the catalyst, however, it is required to be present in a molar amount of 0.5 to 2 times the amount of TMBQ.

With the known catalysts comprising copper and halogen ions as described above, satisfactory yields and selectivity can be obtained only under limited conditions. Therefore, they are unsuitable for practical use.

Japanese Patent Application Laid-Open No. 93931/1975 discloses an improved method over the method of Japanese Patent Publication No. 17585/1978. This method avoids the adverse influence water exerts on the reaction, allows the reaction to proceed efficiently even in water-containing solvents, and makes it easy to repeatedly use the catalyst. This method is intended to prevent deterioration of the catalyst and to allow for repeated use of the copper halide dissolved in an aqueous phase as a catalyst without application of any treatment, by adding to the reaction system, in advance or intermittently, halogen or halogenated compounds capable of releasing halogen into the reaction system, such as bromine, chlorine, hydrogen halide, hypohalogenous acid salts, and 4-bromo-2,3,6-trimethylphenol. As will be apparent from the examples as described hereinafter, such halogen compounds are consumed and diminished at a considerably earlier stage of their repeated use. It is necessary, therefore, to supplement the halogen compounds from time to time. This is troublesome in the operation and increases costs in the industrial production of TMBQ.

Furthermore, in all the known techniques, it is essential to use organic solvents which are completely soluble in water. Therefore, in the separation of the desired TMBQ after the reaction, the operation of separating TMBQ from the catalyst and solvent becomes complicated. Furthermore, other operations such as concentration, dehydration, and purification are needed in the repeated use of the catalyst and solvent. This increases the amount of energy consumed.

SUMMARY OF THE INVENTION

The present invention avoids the above-described problems of the prior art, and has as its objective to provide a process for the production of TMBQ which is markedly superior to conventional processes.

The present invention, in an embodiment thereof, relates to a process for producing 2,3,5-trimethylbenzoquinone which comprises contacting 2,3,6-trimethylphenol with molecular oxygen in a medium consisting of water and an aliphatic alcohol having from 5 to 10 carbon atoms in the presence as catalyst, of a copper halogeno complex having the following formula:

$M_l[Cu(II)_mX_n]_p \cdot ps$ wherein M is an alkali metal or ammonium, Cu(II) is a divalent copper, X is a halogen atom, l is an integer of from 1 to 3, m is 1 or 2, n is an integer of from 3 to 8, p is 1 or 2, and $l+2mp=np$.

The copper halogeno complex may or may not contain water of crystallization.

In another embodiment, the present invention relates to a process for producing 2,3,5-trimethylbenzoquinone which comprises contacting 2,3,6-trimethylphenol with molecular oxygen in a medium consisting of water and an aliphatic alcohol having from 5 to 10 carbon atoms in the presence as catalyst, of a copper halogeno complex of the same formula as described above and an alkali metal halide.

In still another embodiment, the present invention relates to a process for preparing TMBQ by contacting TMP with oxygen gas or an oxygen-containing gas having an oxygen concentration of at least 20% in an aqueous solution of a copper halogeno complex catalyst of the same formula as described above and an alkali metal halide, wherein the catalytic reaction of TMP with the oxygen gas or oxygen-containing gas is carried out semi-batchwise while continuously adding a solution of TMP in an aliphatic alcohol having from 5 to 10 carbon atoms to the aqueous solution of the catalyst to which an aliphatic alcohol having from 5 to 10 carbon atoms, cupric hydroxide, cuprous chloride, or a mixture thereof have previously been added.

BRIEF DESCRIPTION OF THE DRAWINGS

FIG. 1 is a graph showing the relation between the concentration of a copper halogeno complex and its visible absorption spectrum;

FIG. 2 is a graph showing the relation between the concentration of a copper halogeno complex and a molar absorption coefficient of visible absorption spectrum; and FIG. 3 is a graph showing the relation between the concentration of halogen and a molar absorption coefficient of visible absorption spectrum.

DETAILED DESCRIPTION OF THE INVENTION

The copper halogeno complexes represented by the formula as described above are used as catalyst in the present invention. These copper halogeno complexes accelerate oxidation of the TMP with oxygen and permit the conversion of TMP into TMBQ with high selectivity. The copper halogeno complex catalyst of the present invention is superior in the rate of reaction and selectivity of TMBQ to the known catalyst system comprising free copper and halogen ions even in the reaction system where water is present and, furthermore, the drop in the activity of the catalyst due to water is scarcely noticeable.

The copper halogeno complex catalyst of the present invention is a novel catalyst, and produces very favorable results in the industrial practice of the process of the present invention; for example, the size of the reactor can be greatly reduced, the space time yield can be increased, and the catalyst can be used repeatedly.

The copper halogeno complex catalyst of the present invention has excellent properties and even when used alone, permits easy oxidation of the TMP with the oxygen and converts the TMP into TMBQ with high selectivity. When, however, the copper halogeno complex catalyst is used in combination with an alkali metal halide, the selectivity of TMBQ is further increased and, furthermore, the rate of reaction is increased. When the reaction is carried out semi-batchwise in the additional presence of cupric hydroxide and in cuprous chloride, the formation of by-products, for example hexamethyl biphenol (hereinafter "HMBP") is substantially completely eliminated with a concomitant increase in the yield of TMBQ.

The copper halogeno complexes as used herein are coordination compounds of copper and halogen, and are represented by the following formula:

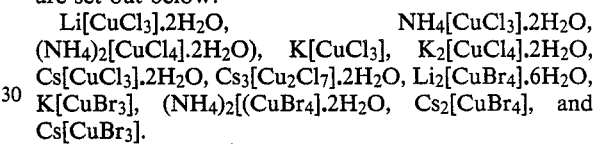

wherein M is an alkali metal or ammonium, Cu(II) is divalent copper, X is halogen, l is an integer of from 1 to 3, m is 1 or 2, n is an integer of from 3 to 8, p is 1 or 2, and $l+2mp=np$. They may or may not contain water of crystallization.

The term alkali metal includes lithium (Li), potassium (K), rubidium (Rb), and cesium (Cs). Of these metals, lithium, potassium, and cesium are preferred. Particularly preferred is lithium. The halogen is preferably chlorine (Cl), bromine (Br), and iodine (I). Particularly preferred are chlorine and bromine.

Typical examples of the copper halogeno complexes are set out below:

Li[CuCl$_3$].2H$_2$O, NH$_4$[CuCl$_3$].2H$_2$O, (NH$_4$)$_2$[CuCl$_4$].2H$_2$O), K[CuCl$_3$], K$_2$[CuCl$_4$].2H$_2$O, Cs[CuCl$_3$].2H$_2$O, Cs$_3$[Cu$_2$Cl$_7$].2H$_2$O, Li$_2$[CuBr$_4$].6H$_2$O, K[CuBr$_3$], (NH$_4$)$_2$[(CuBr$_4$].2H$_2$O, Cs$_2$[CuBr$_4$], and Cs[CuBr$_3$].

These copper halogeno complexes can be prepared by known procedures, for example the methods described in *Mellor's Comprehensive Treatment on Inorganic and Theoretical Chemistry*, Vol. III, pages 182–201 (Longman).

The copper halogeno complexes thus prepared can be identified by known techniques such as by determining their melting points. For example, the copper chloride-lithium complex, Li[CuCl$_3$].2H$_2$O, is red brown in color and is different in appearance from cupric chloride, CuCl$_2$.2H$_2$O, which is a green crystal, and the melting point of the complex is 130°–135° C. According to the above-described reference, *Mellor's Comprehensive Treatment on Inorganic and Theoretical Chemistry*, Vol. III, pages 184 and 169 (Longman), the melting points of a copper chloride-lithium complex, Li[CuCl$_3$].2H$_2$O, and cupric chloride, CuCl$_2$.2H$_2$O, are 130° C. and 110° C., respectively.

In visible absorption spectra of an aqueous copper halogeno complex solution and an aqueous cupric chloride solution, the maximum absorption peaks are between 820 and 880 nm. As the concentration of the copper halogeno complex or cupric chloride increases, the maximum absorption peak shifts to the longer wavelengths side (FIG. 1). Wavelengths at which the maximum absorption peak appears are measured for the copper halogeno complex and cupric chloride at the same concentration and have been proved to be materially different from each other. When the molar absorption coefficient at a wavelength of 800 nm is plotted against the concentration, the molar absorption coefficient being plotted on a logarithmic scale (log ε), it can be seen that the molar absorption coefficient for cupric chloride saturates at concentrations of 3 moles per liter (mol/l) or more, the maximum molar absorption coefficient being 1.45, whereas the molar absorption coefficient for $Li[CuCl_3]\cdot 2H_2O$, for example, saturates at concentrations of 3 mol/l or more, the maximum molar absorption coefficient being 1.52; that is, their molar absorption coefficients are materially different from each other (FIG. 2).

When lithium chloride is dissolved in a saturated solution of $Li[CuCl_3]\cdot 2H_2O$, the molar absorption coefficient approaches 1.63 (FIG. 3). When a combination of a copper chloride lithium complex, $Li[CuCl_3]\cdot 2H_2O$, and lithium chloride is used, it is preferred that the molar absorption coefficient (log ε) of an aqueous solution of the combination be from 1.4 to 1.63.

The pH of an aqueous copper halogeno complex solution varies depending on the concentration of the copper halogeno complex therein but usually is 3.0 or less. Surprisingly it has been found that if an alkali metal halide is dissolved in the aqueous copperhalogeno complex solution, the pH value drops further almost in proportion to the amount of the alkali metal halide added. This tendency does not change even if an alcohol is added to the solution.

The pH of an aqueous solution of the copper halogeno complex catalyst of the present invention is usually 2.5 or less and preferably from 2 to 2.5. In the case where an alkali metal halide is used in combination with the copper halogeno complex, the pH of an aqueous solution of copper halogeno complex and alkali metal halide is usually 2 or less and preferably from 2 to −1, with the range of from 1 to −0.5 being most preferred.

Alkali metal halides which can be used in combination with the copper halogeno complexes of the present invention include:

NaCl, LiCl, KCl, CsCl, NaBr, $NH_4Br$, KBr, CsBr, NaI, LiI, KI, CsI, etc. Of these compounds, lithium chloride (LiCl) is especially preferred from the viewpoint of yield and rate of reaction. The catalyst composed mainly of the copper halogeno complex and the alkali metal halide is hereinafter referred to as "copper halogeno complex/alkali metal halide catalyst".

In the practice of the process of the present invention, in general, a copper halogeno complex or a mixture of a copper halogeno complex and an alkali metal halide is dissolved in a predetermined amount of water in a predetermined proportion to prepare a copper halogeno complex or copper halogeno complex/alkali metal halide catalyst of the present invention, an aliphatic alcohol having 5 to 10 carbon atoms and TMP are added, and then the TMP is contacted with oxygen in the presence of the catalyst.

In the case where alkali metal halides are used in combination, the ratio of alkali metal halide to copper halogeno complex in the copper halogeno complex/alkali metal halide catalysts is one of the significant factors exerting influences on the oxidation of the TMP. In general, if the ratio of alkali metal halide to copper halogeno complex is too large, the rate of reaction is undesirably reduced, whereas if it is too small, the effect of addition of the alkali metal halide cannot be obtained, although it varies depending on the type of the copper halogeno complex and alkali metal halide. In addition, the proportion of the alkali metal halide used is limited by its solubility in the reaction system. Thus, although the molar ratio of alkali metal halide to copper halogeno complex cannot be determined unconditionally, it is usually from 1 to 15, preferably from 1 to 10, and most preferably from 2 to 5.

The concentration of the copper halogeno complex in the aqueous phase of the reaction system exerts a great influence on the yield and rate of reaction. That is, the amount of water added to the reaction system is one of the most important factors for efficiently carrying out the reaction. From a viewpoint of efficiency of the reaction, it is preferred that the concentration of the copper halogeno complex/alkali metal halide catalyst in the aqueous phase be high. If the concentration of the copper halogeno complex in the aqueous phase is 20% by weight or less, the selectivity of TMBQ seriously drops. The concentration of the copper halogeno complex in the aqueous phase (excluding the alcohol), taking into consideration its solubility, is 20 to 80% by weight, preferably from 20 to 70% by weight, more preferably from 20 to 60% by weight, and most preferably from 30 to 60% by weight.

In the case of the copper halogeno complex/alkali metal halide catalyst, the concentration of the mixture of the copper halogeno complex and the alkali metal halide in the aqueous phase of the reaction system also exerts a considerable influence on the yield and rate of reaction. That is, also in this case, the amount of water added to the reaction system is one of the most important factors for efficiency of the reaction. From a viewpoint of efficiency of the reaction, it is preferred that the concentration of the copper halogeno complex/alkali metal halide catalyst be as high as possible. If the concentration of the mixture of the copper halogeno complex and the alkali metal halide in the aqueous phase is 20% by weight or less, the selectivity of TMBQ drops considerably. The concentration of the mixture of the copper halogeno complex and the alkali metal halide in the aqueous phase (excluding alcohol), taking into consideration also its solubility, is preferably from 20 to 80% by weight, more preferably from 20 to 70% by weight, and most preferably from 20 to 60% by weight.

The optimum amount of the copper halogeno complex used is determined by both the yield and rate of reaction. That is, there is a tendency that if the amount of the copper halogeno complex used is too small, the yield of TMBQ is small and the rate of reaction is also low. On the other hand, even if the copper halogeno complex is used in amounts in excess of a certain level, no additional effect is realized and, therefore, addition of such large amounts of the copper halogeno complex is of no value. The amount of the copper halogeno complex used in the present invention varies with the type of the copper halogeno complex and cannot be determined unconditionally. In general, in the case of the copper halogeno complex catalyst, the copper halogeno complex is used in an amount of from 0.1 to 5 moles, preferably from 0.5 to 3 moles, and most preferably from 1 to 2 moles per mole of TMP. This can be applied also to the copper halogeno complex/alkali metal halide catalyst.

In accordance with a basic embodiment of the present invention, the reaction is carried out in the presence of oxygen by adding a solution of TMP in a suitable alcohol solvent to a catalyst solution previously adjusted to a given composition and a given concentration at a given dropping rate.

In the embodiment, the amounts of the copper halogeno complex and alkali metal halide used cannot be determined unconditionally because they vary depending on the type of the copper halogeno complex used, but it is preferred that the amount of the catalyst used is less than that used in the batchwise reaction system. If the amount of the catalyst used is indicated in terms of the amount of the copper halogeno complex, the amount of the copper halogeno complex used is 0.1 to 1 mole, preferably 0.1 to 0.5 mole, and especially preferably 0.1 to 0.3 mole per mole of the total amount of TMP continuously added to the reaction system.

The amount of the catalyst used in the above system is very small compared with that in the batchwise system. The amount of the catalyst used in the above system to provide the same yield of TMBQ as obtained under the optimum conditions of the batchwise system is about ¼ of that in the batchwise system.

The medium as used herein is heterogeneous since the alcohols having from 5 to 10 carbon atoms are immiscible or only slightly miscible with water. Thus the process of the present invention is carried out in a heterogeneous reaction system. In accordance with the present invention, therefore, the catalyst can be recycled and used repeatedly, and the reaction product can be separated efficiently.

The alcohols as used herein are aliphatic alcohols having from 5 to 10 carbon atoms because of their insolubility in water. Preferred examples of aliphatic alcohols which can be used in the present invention include n-amyl alcohol, isoamyl alcohol, n-hexyl alcohol, 2-ethylhexanol, n-heptyl alcohol, n-octyl alcohol, n-nonyl alcohol, and n-decyl alcohol.

The medium as used herein is effective in dissolving the copper halogeno complex, both copper halogeno complex and alkali metal halide, and the copper halogeno complex, alkali metal and cupric hydroxide and/or cuprous chloride, the TMP starting material, and also oxygen. Thus, the desired TMBQ can be produced very efficiently only by contacting these solutions.

According to the present invention, aliphatic alcohols having from 5 to 10 carbon atoms are used, and the reaction system is completely heterogeneous. Surprisingly, however, it has been found that the reaction proceeds efficiently even in such a heterogeneous condition. After the reaction is completed, the reaction mixture is composed of an aqueous phase as a catalyst layer and an organic phase as an alcohol layer containing the TMBQ. Thus the catalyst and TMBQ can be easily separated by applying phase separation. This is very advantageous since post treatment for reuse of the catalyst and recovery of the TMBQ is very much simplified.

The amount of the alcohol used is determined taking into consideration the dissolution of TMP and the ratio of alcohol to water used. It is necessary for the alcohol to be used in such an amount as not to allow the TMP to crystallize particularly in the case where the solution of TMP in the alcohol has to be fed to the reaction system quantitatively and continuously. Taking into consideration the above factor and also the reaction efficiency, for example, the amount of the alcohol used can be determined appropriately. In general, the alcohol is used in such an amount that the connection of TMP in the alcohol is from 5 to 50%, preferably from 10 to 50%, and especially preferably from 10 to 30%.

The weight of alcohol to water is from 0.01 to 20, preferably from 0.05 to 5. In other words, the weight ratio of water to alcohol is from 0.05 to 100, preferably from 0.2 to 20.

The reaction temperature varies over wide ranges depending on the type and amount of each of the copper halogeno complex or copper halogeno complex and alkali metal halide, the amount of water and the alcohol used. In general, the reaction temperature is preferably from 10° to 120° C., more preferably from 30° to 100° C., and most preferably from 40° to 80° C. In the batchwise system, as the reaction scale is increased, it becomes more difficult to remove the reaction heat, and there is a danger of the reaction running away. On the contrary, in the semi-batchwise reaction system of the present invention, the amount of the reaction heat per unit hour can be controlled by controlling the speed of feeding the starting material, TMP, and thus the reaction heat is easier to remove, which in turn makes it easier to control the reaction temperature.

The reaction time varies over wide ranges depending on the type and amount of the copper halogeno complex and alkali metal halide, the reaction temperature, the amount of water used, the alcohol, etc. In general, the reaction time is from about 5 to about 300 minutes.

The starting material, TMP, used in the present invention is not limited by its method of preparation. For example, TMP prepared by alkylation of phenols (e.g. alkylation of m-cresol, 2,3-xylenol, and 2,5-xylenol), transalkylation of polymethyl phenol, alkali-fusion of 2,3,6-trimethylbenzenesulfonic acid, oxidation of 2,3,6-trimethylcumene, fractionation of tars, and by isolation from phenols can be used.

The term oxygen as used herein includes both pure oxygen and oxygen-containing gases. These oxygen-containing gases include oxygen-rich air, air, and oxygen diluted with an inert gas. Inert gases which can be used to dilute the oxygen include nitrogen, helium and argon. The concentration of oxygen in the gas is preferably from 20 to 100%.

The reaction pressure is an oxygen partial pressure and is from 0.05 to 50 $kg/cm^2$, preferably from 0.1 to 20 $kg/cm^2$, more preferably from 0.2 to 10 $kg/cm^2$, more preferably from 0.3 to 3 $kg/cm^2$, and most preferably from 0.3 to 1 $kg/cm^2$ (absolute pressure).

TMBQ is produced by contacting the TMP with oxygen in the presence of the copper halogeno complex or copper halogeno complex/alkali metal halide or copper halogeno complex/alkali metal halide/cupric hydroxide and/or cuprous chloride catalyst in the mixed solvent of water and alcohol. In the most preferred embodiment of the present invention, an agitation-type reactor is used, since it permits efficient contact between gas and liquid.

The TMP can be contacted with oxygen by techniques such as a method of passing oxygen through the reactor and a gas circulation method in which oxygen absorbed is compensated by supplying fresh oxygen to maintain the pressure at a given level.

The process of the present invention can be carried out in a batch system, a semi-batch system, or in a continuous flow system.

The process of the present invention produces various advantages. For example, since copper halogeno complexes as defined above are used as the catalyst, TMP can be easily oxidized with oxygen and TMBQ can be formed in high yields and high selectivities. Addition of alkali metal halides as also defined above permits a further increase in the selectivity and thereby increases the yield by about 10%.

In the preparation of TMBQ through the oxidation of TMP with the catalyst comprising the copper halogeno complex and alkali metal halide, if a batchwise reaction system is employed, HMBP is formed to some extent. The formation of this HMBP can be depressed and the yield of TMBQ increased and additionally the use of an oxygen gas of low concentration made possible if the relationship between the oxidation reaction rate and the feeding rate of the TMP is controlled. In the case where the feeding rate of TMP is higher than the rate at which TMP is oxidized, the mode of the reaction becomes similar to the batchwise system. As a result, the amount of HMBP formed is increased somewhat and the advantage of the semi-batchwise reaction system is lost. In a case where the feed rate of the TMP is lower than the oxidation rate of the TMP, the amount of HMBP formed is smaller and the features of the semi-batchwise reaction system are realized. However, if the feed rate of the TMP is decreased excessively, the reaction time is markedly lengthened and thus the space time yield is undesirably decreased. In a preferred embodiment of the present invention, therefore, the oxidation reaction rate is made equal to the feed rate of TMP, or the feed rate of the TMP is maintained lower than the oxidation reaction rate. The oxidation reaction rate varies with the reaction temperature, the type and amount of the catalyst, and so forth. The feed rate of the TMP can be determined experimentally The TMP is fed into the reaction usually over 2 to 10 hours, preferably over 2 to 8 hours, and most preferably over 3 to 5 hours.

In the reaction of the present invention, as above set out even after the introduction of the TMP is completed, a small amount of 4-chlorotrimethylphenol (hereinafter "Cl-TMP"), an intermediate reaction product of TMBQ, remains in the reaction system, and it is necessary for the oxidation reaction to be further continued. The time for this purpose cannot be determined unconditionally because it varies depending on other reaction conditions. In general, it is from 0.5 to 5 hours and preferably from 1 to 3 hours.

In the most basic embodiment of the semi-batchwise reaction, a solution of the TMP dissolved in a suitable solvent in a suitable concentration is supplied to a previously prepared aqueous catalyst solution at a suitable feed rate in the presence of an oxygen-containing gas having an oxygen concentration of at least 20%. In this case, however, there is an induction period at the initial stage of the reaction although this is not as significant when 100% oxygen is used. For this reason, the reaction proceeds nearly batchwise at the initial stage thereof for a relatively short period of time, thereby increasing the amount of HMBP formed and decreasing the TMBQ yield. This tendency becomes more marked as the concentration of oxygen in the gas is further reduced and, furthermore, the oxidation reaction rate drops. Therefore, in the instance where the concentration of oxygen in the gas used in small, it is necessary to decrease the feed rate of the TMP, thereby depressing the formation of HMBP, so as to increase the TMBQ yield. This, however, is undesirable because the reaction time is excessively increased.

In the process of the present invention, therefore, the same alcohol solvent as used in the preparation of the TMP solution, cupric hydroxide, cuprous chloride, or a mixture thereof is previously added to the reaction system, so that the induction period of the reaction can be avoided and the oxidation reaction can be carried out satisfactorily even if an oxygen-containing gas having an oxygen concentration of about 20%, i.e., air, is used. In the case where the alcohol solvent is added to the reaction system prior to the oxidation reaction of TMP, the amount of the alcohol added is from 0.05 to 1.3 times, preferably from 0.05 to 0.65 times, and most preferably from 0.13 to 0.26 times the weight of the alcohol solvent contained in the entire TMP solution. The amount of cupric hydroxide or cuprous chloride used is limited by its solubility in the reaction system. In general, the amount of cupric hydroxide or cuprous chloride used is from 0.01 to 0.05 mole per mole of the copper halogeno complex.

The induction period at the initial state of the reaction can thereby be eliminated, by adding the alcohol solvent, cupric hydroxide, cuprous chloride, or a mixture thereof. In the case where the cupric hydroxide and/or cuprous chloride is used, the rate of oxidation of Cl-TMP to TMBQ remaining in the reaction system after the dropwise addition of the starting material is increased and, as a result, the total reaction time is desirably shortened.

In accordance with the aforesaid embodiment of the invention, a mixture of the copper halogeno complex and alkali metal halide is used as catalyst, an aliphatic alcohol having from 5 to 10 carbon atoms, cupric hydroxide, cuprous chloride or a mixture thereof is previously added to the aqueous catalyst solution, and the reaction is carried out semi-batchwise. Compared with the batchwise reaction system, the amount of catalyst used can be greatly reduced, the yield of TMBQ can be increased, and furthermore the control of the reaction temperature can be facilitated.

Irrespective of the fact that the process of the present invention is carried out in a reaction system containing water, the process of the present invention is superior in the rate of reaction and selectivity of TMBQ to conventional processes using the known catalyst system comprising free copper and halogen ions. Furthermore, the process of the present invention has a surprising feature that the drop in the activity of the catalyst due to water is scarcely observed. Thus, the process of the present invention is very useful in the industrial production of TMBQ from TMP.

TMBQ, the product of the present invention, can be easily separated and recovered. The reason is, as described above, that since aliphatic alcohols having from 5 to 10 carbon atoms immiscible or only slightly miscible with water are used, the reaction mixture can be easily separated into an aqueous phase, i.e., catalyst layer, and an organic phase, i.e., alcohol layer containing TMBQ. The TMBQ can be recovered by distilling away the alcohol from the alcohol layer, and the aqueous or catalyst layer can be used repeatedly, as such or if necessary, after concentration and/or purification.

The alcohols used in the present invention are readily available at a low price. Thus the process of the present invention is industrially markedly superior to the conventional processes.

The alcohol layer thus obtained contains substantially no by-products. When it is washed with water and then reduced as such, a precursor for vitamin E, 2,3,5-trimethylhydroquinone, is obtained in a high degree of purity.

The present invention is described in greater detail with reference to the following examples and comparative examples. In the examples and comparative examples, all conversions and yields are expressed in terms of moles.

EXAMPLES 1 TO 8 AND COMPARATIVE EXAMPLE 1

A 100-milliliter four-necked flask was charged with 3.4 grams (25 millimoles) of TMP, 4.3 grams (25 millimoles) of $CuCl_2.2H_2O$ or 25 millimoles of a previously prepared copper halogeno complex as shown in Table 1, 10 milliliters of n-hexyl alcohol, and a predetermined amount of water as shown in Table 1.

After replacement of the atmosphere in the flask with oxygen, the mixture was maintained at 60° C. by external heating or cooling and vigorously stirred at 800 revolutions per minute (rpm). Oxygen was successively introduced into the flask from a gas holder, and the amount of oxygen consumed was measured by means of a gas biuret. When the absorption of oxygen gas stopped, the reaction was taken as completed.

The alcohol layer, after separation from the water layer, was analyzed by gas chromatography. The results are shown in Table 1.

TABLE 1

| Run No. | Catalyst | Amount of Water (milliliters) | Rate of Absorption of Oxygen (% per hour) | Conversion of TMP (%) | Yield of TMBQ (%) |
|---|---|---|---|---|---|
| 1 (Example 1) | Complex A | 10 | 260 | 100 | 80.0 |
| 2 (Example 2) | Complex B | 10 | 150 | 100 | 79.0 |
| 3 (Example 3) | Complex C | 10 | 115 | 100 | 83.5 |
| 4 (Example 4) | Complex D | 10 | 93 | 100 | 80.0 |
| 5 (Example 5) | Complex E | 15 | 95 | 100 | 83.0 |
| 6 (Example 6) | Complex F | 10 | 87 | 100 | 79.5 |
| 7 (Example 7) | Complex G | 15 | 86 | 100 | 82.0 |
| 8 (Example 8) | Complex H | 15 | 89 | 100 | 83.1 |
| 9 (Comparative Example 1) | $CuCl_2.2H_2O$ | 10 | 80 | 100 | 69.4 |

Note:
Complex A: $Li[CuCl_3].2H_2O$
Complex B: $(NH_4)[CuCl_3].2H_2O$
Complex C: $(NH_4)_2[CuCl_4].2H_2O$
Complex D: $K[CuCl_3]$
Complex E: $K_2[CuCl_4].2H_2O$
Complex F: $Cs[CuCl_3]$
Complex G: $Cs_2[CuCl_4]$
Complex H: $Cs_2[CuBr_4]$ Rate of Absorption of Oxygen ... $\frac{\text{Amount of oxygen absorbed per hour}}{\text{Theoretical amount of oxygen absorbed}} \times 100$

EXAMPLES 9 TO 11

The procedure of Example 1 was repeated using 3.4 grams (25 millimoles) of TMP, 25 millimoles of a previously prepared copper halogeno complex as shown in Table 2, 10 milliliters of n-octyl alcohol, and 10 milliliters of water.

The results are shown in Table 2.

After the reaction, the reaction mixture separated into a water layer and an alcohol layer. The water layer (catalyst layer), after separation from the alcohol layer, could be recycled and reused.

TABLE 2

| Run No. | Copper Halogeno Complex | Amount of water (milliliters) | Rate of Absorption of Oxygen (% per hour) | Conversion of TMP (%) | Yield of TMBQ (%) |
|---|---|---|---|---|---|
| 1 (Example 9) | Complex B | 10 | 160 | 100 | 81.0 |
| 2 (Example 10) | Complex E | 15 | 150 | 100 | 80.5 |
| 3 (Example 11) | Complex G | 15 | 80 | 100 | 82.8 |

Note:
Complexes B, E and G, and Rate of Absorption of Oxygen: Same as described in Table 1.

EXAMPLES 12 AND 13

The procedure of Example 1 was repeated using 3.4 grams (25 millimoles) of TMP, a predetermined amount of a previously prepared copper halogeno complex, $Li[CuCl_3].2H_2O$, as shown in Table 3, 10 milliliters of water, and 10 milliliters of n-hexyl alcohol were used.

The results are shown in Table 3.

After the reaction, the reaction mixture separated into a water layer and an alcohol layer. The water layer (catalyst layer), after separation from the alcohol layer, could be recycled and reused.

TABLE 3

| Run No. | Complex (grams (millimoles)) | Rate of Absorption of Oxygen (% per hour) | Conversion of TMP (%) | Yield of TMBQ (%) |
|---|---|---|---|---|
| 1 (Example 12) | 6.6 (50) | 230 | 100 | 84.1 |
| 2 (Example 13) | 15.9 (75) | 130 | 100 | 83.5 |

Note:
Rate of Absorption of Oxygen ... Same as described in Table 1.

EXAMPLES 14 TO 16

The procedure of Example 1 was repeated using 3.4 grams (25 millimoles) of TMP, 5.3 grams (25 millimoles) of a copper halogeno complex, $Li[CuCl_3].2H_2O$, 10 milliliters of water, and 10 milliliters of an alcohol as shown in Table 4.

The results are shown in Table 4.

After the reaction, the reaction mixture separated into a water layer and an alcohol layer. The water layer (catalyst layer), after separation from the alcohol layer, could be recycled and reused.

TABLE 4

| Run No. | Alcohol | Rate of Absorption of Oxygen (% per hour) | Conversion of TMP (%) | Yield of TMBQ (%) |
|---|---|---|---|---|
| 1 (Example 14) | i-Amyl alcohol | 230 | 100 | 80.1 |
| 2 (Example 15) | n-Octyl alcohol | 230 | 100 | 80.4 |
| 3 (Example 16) | n-Decyl alcohol | 200 | 100 | 80.0 |

TABLE 4-continued

| Run No. | Alcohol | Rate of Absorption of Oxygen (% per hour) | Conversion of TMP (%) | Yield of TMBQ (%) |
|---|---|---|---|---|
| ple 16) | | | | |

Note:
Rate of Absorption of Oxygen ... Same as described in Table 1.

EXAMPLES 17 AND 18

The procedure of Example 1 was repeated wherein 3.4 grams (25 millimoles) of TMP, 5.3 grams (25 millimoles) of a copper halogeno complex, Li[CuCl$_3$].2H$_2$O, 10 milliliters of water, and 10 milliliters of n-hexyl alcohol were used and the reaction temperature was changed as shown in Table 5.

The results are shown in Table 5.

After the reaction, the reaction mixture separated into a water layer and an alcohol layer. The water layer (catalyst layer), after separation from the alcohol layer, could be recycled and reused.

TABLE 5

| Run No. | Reaction Temperature (°C.) | Time required till Gas Absorption stops (minutes) | Conversion of TMP (%) | Yield of TMBQ (%) |
|---|---|---|---|---|
| 1 (Example 17) | 80 | 35 | 100 | 78.8 |
| 2 (Example 18) | 40 | 213 | 100 | 75.8 |

EXAMPLE 19

A 200-milliliter four-necked flask was charged with 6.8 grams (50 millimoles) of TMP, 10.6 grams (50 millimoles) of a copper halogeno complex, Li[CuCl$_3$].2H$_2$O, 20 milliliters of n-octyl alcohol, and 20 milliliters of water. The reaction was conducted for 1 hour in the same manner as set out in Example 1. After the reaction was completed, the reaction mixture was separated into an organic layer and a water layer. The organic layer was analyzed by gas chromatography to determine the conversion of TMP and the yield of TMBQ. The water layer was returned to the four-necked flask. Then, 6.8 grams of TMP and n-octyl alcohol were introduced in the four-necked flask and reacted. This operation was repeated several times and deterioration of the catalyst was examined.

The results are shown in Table 6.

TABLE 6

| Run No. | Number of Operations repeated | Conversion of TMP (%) | Yield of TMBQ (%) |
|---|---|---|---|
| 1 | 1 | 100 | 76.1 |
| 2 | 2 | 99.9 | 80.3 |
| 3 | 3 | 99.9 | 75.1 |
| 4 | 4 | 99.8 | 78.3 |
| 5 | 5 | 99.8 | 79.1 |
| 6 | 6 | 99.8 | 80.2 |
| 7 | 7 | 99.8 | 80.5 |
| 8 | 8 | 100 | 80.8 |
| 9 | 9 | 99.8 | 78.1 |
| 10 | 10 | 99.8 | 78.0 |
| 11 | 11 | 99.9 | 79.6 |

EXAMPLES 20, 21 AND COMPARATIVE EXAMPLE 2

The procedure of Example 1 was repeated wherein 3.4 grams (25 millimoles) of TMP, 5.3 grams (25 millimoles) of a copper halogeno complex, Li[CuCl$_3$].2H$_2$O, and 10 milliliters of n-hexyl alcohol were used and the amount of water was changed as set out in Table 7.

The results are shown in Table 7.

TABLE 7

| Run No. | Amount of water (milliliters) | Concentration of Complex in the Aqueous Phase (% by weight) | Rate of Absorption of Oxygen (% per hour) | Conversion of TMP (%) | Yield of TMBQ (%) |
|---|---|---|---|---|---|
| 1 (Example 20) | 5 | 43 | 200 | 100 | 81.0 |
| 2 (Example 21) | 15 | 22 | 230 | 100 | 79.9 |
| 3 (Comparative Example 2) | 20 | 17 | 150 | 100 | 69.5 |

COMPARATIVE EXAMPLE 3

A mixture of 25 millimoles of a copper chloride/lithium complex, Li[CuCl$_3$].2H$_2$O, 10 milliliters of water, 10 milliliters of n-hexylalcohol, and 2.4 grams (25 millimoles) of phenol was placed in a four-necked flask and reacted with stirring under the same conditions as in Example 1. Four hours after the start of the reaction, the reaction mixture was treated in the same manner as in Example 1 and analyzed by gas chromatography.

The results were as follows:

| | |
|---|---|
| Conversion of phenol | 82.2% |
| Yield of o-chlorophenol | 3.0% |
| Yield of p-chlorophenol | 27.0% |
| Yield of dichlorophenol | 0.5% |

Any other compound could not be detected by the gas chromatography analysis.

EXAMPLES 22 TO 25, REFERENCE EXAMPLES I TO IV, AND COMPARATIVE EXAMPLE 4

A mixture of 25 millimoles of a previously prepared crystalline copper halogeno complex or commercially available copper halogeno complex and 75 millimoles of an alkali metal halide was placed in a four-necked flask. Then, 10–20 milliliters of water was added to the mixture which was then stirred to prepare a catalyst solution.

Thereafter, 3.4 grams (25 millimoles) of TMP and 10 milliliters of n-octyl alcohol were introduced into the flask.

After replacement of the atmosphere in the flask with oxygen, the mixture was maintained at 60° C. and vigorously stirred at 800 rpm. Oxygen was successively introduced from a gas holder and the amount of oxygen consumed was measured by the use of a gas biuret. When the absorption of oxygen had ceased, the reaction was taken as completed. After the reaction was completed, the reaction mixture was separated into an organic alcohol layer and a water layer. The organic layer was analyzed by gas chromatography.

The results are shown in Table 8.

TABLE 8

| Run No. | Catalyst Complex | Catalyst Chloride | Amount of water (milliliters) | Conversion of TMP (%) | Yield of TMBQ (%) | Yield of HMBP (%) | Rate of Absorption of Oxygen (% per hour) |
|---|---|---|---|---|---|---|---|
| 1 (Example 22) | A | LiCl | 10 | 100 | 95 | 4 | 370 |
| 2 (Reference Example I) | A | — | 10 | 100 | 80 | 15 | 250 |
| 3 (Example 23) | B | LiCl | 10 | 100 | 85 | 5.4 | 180 |
| 4 (Reference Example II) | B | — | 10 | 100 | 80 | 12 | 150 |
| 5 (Example 24) | C | KCl | 15 | 100 | 83 | 9 | 130 |
| 6 (Reference Example III) | C | — | 15 | 100 | 79 | 11 | 110 |
| 7 (Example 25) | D | CsCl | 20 | 100 | 85 | 9 | 95 |
| 8 (Reference Example IV) | D | — | 20 | 100 | 81 | 13 | 90 |
| 9 (Comparative Example 4) | — | $CuCl_2$ | 10 | 100 | 69.1 | 18 | 80 |

Note:
Compexes A to D ... Same as described in Table 1.
$CuCl_2$ ... $CuCl_2$/TMP (molar ratio) = 1/1
HMBP ... Hexamethylbiphenol
Rate of absorption of oxygen ... Same as described in Table 1.

EXAMPLES 26 TO 34

The procedure of Example 22 was repeated using 25 millimoles of TMP, predetermined amounts of a copper halogeno complex, $Li[CuCl_3].2H_2O$, and LiCl as shown in Table 9, 10 milliliters of n-octyl alcohol, and 10 milliliters of water.

The results are shown in Table 9.

After the reaction, the reaction mixture separated into a water layer and an alcohol layer. The water layer (catalyst layer), after separation from the alcohol layer, could be recycled and reused.

EXAMPLES 35, 36 AND COMPARATIVE EXAMPLE 5

The procedure of Example 22 was repeated using 25 millimoles of TMP, 25 millimoles of a previously prepared crystalline complex, $Li[CuCl_3].2H_2O$, 75 millimoles of LiCl, and 10 milliliters of n-hexanol and the amount of water added was changed as shown in Table 10.

The results are shown in Table 10.

After the reaction, the reaction mixture separated into a water layer and an alcohol layer. The water layer (catalyst layer), after separation from the alcohol layer, could be recycled and reused.

TABLE 10

| Run No. | Amount of Water used (grams) | Concentration of Catalyst (% by weight) | pH of Catalyst layer | Conversion of TMP (%) | Yield of TMBQ (%) | Yield of HMBP (%) | Rate of Absorption of Oxygen (% per hour) |
|---|---|---|---|---|---|---|---|
| 1 (Example 35) | 15 | 34 | −0.6 | 100 | 91 | 8 | 180 |
| 2 (Example 36) | 20 | 28 | 0.1 | 100 | 89 | 10 | 150 |
| 3 (Comparative Example 5) | 40 | 16 | 2.6 | 100 | 70 | 15 | 100 |

Note:
Rate of absorption of oxygen ... Same as described in Table 1.

EXAMPLES 37 TO 42

The procedure of Example 22 was repeated using 25 millimoles of TMP, 25 millimoles of a previously prepared crystalline complex, $Li[CuCl_3].2H_2O$, and 75

TABLE 9

| Run No. | $Li(CuCl_3)$/LiCl/TMP (molar ratio) | Conversion of TMP (%) | Yield of TMBQ (%) | Yield of HMBP (%) | Yield of 4-Cl-TMP (%) | Rate of Absorption of Oxygen (% per hour) |
|---|---|---|---|---|---|---|
| 1 (Example 26) | 0.14/0.14/1 | 100 | 85 | 8 | 1 | 90 |
| 2 (Example 27) | 0.14/0.7/1 | 100 | 81 | 8 | 4 | 85 |
| 3 (Example 28) | 0.5/3.5/1 | 100 | 89 | 7 | Trace | 180 |
| 4 (Example 29) | 0.5/7.5/1 | 100 | 87 | 3 | Trace | 95 |
| 5 (Example 30) | 1/5/1 | 100 | 96 | 3 | Trace | 310 |
| 6 (Example 31) | 1/7/1 | 100 | 96 | 1 | Trace | 100 |
| 7 (Example 32) | 2.5/4.5/1 | 100 | 92 | 8 | Trace | 90 |
| 8 (Example 33) | 2.5/7.5/1 | 100 | 95 | 4 | Trace | 90 |
| 9 (Example 34) | 2.5/12.5/1 | 100 | 96 | 3 | Trace | 90 |

Note:
Rate of absorption of oxygen ... Same as definad in Table 1.

millimoles of LiCl but the type of the alcohol used was varied as set out in Table 11.

The results are shown in Table 11.

After the reaction, the reaction mixture separated into a water layer and an alcohol layer. The water layer (catalyst layer), after separation from the alcohol layer, could be recycled and reused.

TABLE 11

| Run No. | Alcohol | Conversion of TMP (%) | Yield of TMBQ (%) | Yield of HMBP (%) | Rate of Absorption of Oxygen (% per hour) |
| --- | --- | --- | --- | --- | --- |
| 1 (Example 37) | n-Amyl alcohol | 100 | 94 | 6 | 320 |
| 2 (Example 38) | n-Hexyl alcohol | 100 | 93 | 7 | 300 |
| 3 (Example 39) | n-Heptyl alcohol | 100 | 95 | 5 | 350 |
| 4 (Example 40) | n-Octyl alcohol | 100 | 95 | 4 | 370 |
| 5 (Example 41) | n-Nonyl alcohol | 100 | 93 | 7 | 260 |
| 6 (Example 42) | n-Decyl alcohol | 100 | 94 | 6 | 250 |

Note:
Rate of Absorption of Oxygen ... Same as described in Table 1.

EXAMPLES 43 TO 47

The procedure of Example 22 was repeated using 25 millimoles of TMP, 25 millimoles of a previously prepared crystalline complex, $Li[CuCl_3].2H_2O$, and 75 millimoles of LiCl, the amount of n-octanol used being varied as set out in Table 12.

The results are shown in Table 12.

After the reaction, the reaction mixture separated into a water layer and an alcohol layer. The water layer (catalyst layer), after separation from the alcohol layer, could be recycled and reused.

TABLE 12

| Run No. | Amount of n-Octanol used (milliliters) | Concentration of TMP in n-Octanol (% by weight) | Conversion of TMP (%) | Yield of TMBQ (%) | Yield of HMBP (%) | Rate of Absorption of Oxygen (% per hour) |
| --- | --- | --- | --- | --- | --- | --- |
| 1 (Example 43) | 5 | 45.3 | 100 | 92 | 8 | 100 |
| 2 (Example 44) | 10 | 29.3 | 100 | 92 | 7 | 310 |
| 3 (Example 45) | 20 | 17.2 | 100 | 93 | 6 | 330 |
| 4 (Example 46) | 30 | 10.2 | 100 | 95 | 4 | 295 |
| 5 (Example 47) | 60 | 5.4 | 100 | 85 | 4 | 250 |

Note:
Rate of Absorption of Oxygen ... Same as described in Table 1.

EXAMPLES 48 TO 52

The procedure of Example 22 was repeated using 25 millimoles of TMP, 25 millimoles of $Li[CuCl_3].2H_2O$, and 90 millimoles of LiCl, and the reaction temperature was changed as shown in Table 13.

The results follow in Table 13.

After the reaction, the reaction mixture separated into a water layer and an alcohol layer. The water layer (catalyst layer), after separation from the alcohol layer, could be recycled and reused.

TABLE 13

| Run No. | Reaction Temperature (°C.) | Conversion of TMP (%) | Yield of TMBQ (%) | Yield of HMBP (%) | Rate of Absorption of Oxygen (% per hour) |
| --- | --- | --- | --- | --- | --- |
| 1 (Example 48) | 50 | 100 | 91.1 | 6 | 250 |
| 2 (Example 49) | 60 | 100 | 94.8 | 5 | 360 |
| 3 (Example 50) | 70 | 100 | 92.3 | 6 | 360 |
| 4 (Example 51) | 80 | 100 | 92.0 | 5 | 340 |
| 5 (Example 52) | 90 | 100 | 91.2 | 4 | 280 |

Note:
Rate of Absorption of Oxygen ... Same as described in Table 1.

COMPARATIVE EXAMPLE 6

A mixture of 2.5 grams (25 millimoles) of cuprous chloride, 4.2 grams (100 millimoles) of lithium chloride, and 20 milliliters of methanol was placed in a four-necked flask and stirred to prepare a uniform catalyst solution.

To this catalyst solution was added 3.4 grams (25 millimoles) of TMP, and the reaction was performed under the same conditions as in Example 22. With a lapse of time, a large amount of brown polymeric material deposited on the inner walls of a reactor and a stirrer. In the course of the reaction, absorption of oxygen was not observed at all. When the oxygen absorption stopped, a large amount of water was added to the reaction mixture while leaving as such the polymeric material deposited. The resulting mixture was extracted with toluene. The extract thus obtained was analyzed by gas chromatography and found to contain only a small amount of TMP. It is believed, therefore, that almost all of TMP reacted was converted into the polymeric material.

COMPARATIVE EXAMPLE 7

A mixture of 25 millimoles of a copper halogeno complex, $Li[CuCl_3].2H_2O$, 75 millimoles of LiCl, and 10 milliliters of water was placed in a four-necked flask and stirred to prepare a catalyst solution.

Then, 2.4 grams (25 millimoles) of phenol and 10 milliliters of n-octylalcohol were introduced into the flask, and the reaction was performed under the same conditions as in Example 22. The time required till the reaction was completed was 4 hours.

The results were as follows:

| Conversion of phenol | 91.1% |
|---|---|
| Yield of o-chlorophenol | 1.7% |
| Yield of p-chlorophenol | 35.6% |
| Yield of dichlorophenol | 1.5% |

The formation of benzoquinone was not observed. Any other compound could not detected by the gas chromatography analysis.

EXAMPLE 53

A 200-milliliter four-necked flask was charged with 6.8 grams (50 millimoles) of TMP, 10.6 grams (50 millimoles) of a copper halogeno complex, Li[CuCl$_3$].2H$_2$O, 6.4 grams (150 millimoles) of lithium chloride, LiCl, 20 milliliters of n-hexanol, and 20 milliliters of water. The reaction was performed for 1 hour in the same manner as in Example 22. After the reaction was completed, the reaction mixture was separated into an organic layer and a water layer.

The organic layer and 200 milliliters of benzene were introduced into the separating funnel, and the funnel was shaken to separate a small amount of water from benzene layer including the organic layer. Thus obtained water was added to the water layer obtained previously. The benzene layer was analyzed by gas chromatography to determine the conversion of TMP and yield of TMBQ. The water layer was returned to the four-necked flask. The, 6.8 grams of TMP and 20 milliliters of n-hexanol were introduced in the four-necked flask and reacted. This operation was repeated several times and deterioration of the catalyst was examined.

The results are shown in Table 14.

TABLE 14

| Run No. | Number of Operations repeated | Conversion of TMP (%) | Yield of TMBQ (%) |
|---|---|---|---|
| 1 | 1 | 100 | 94.8 |
| 2 | 2 | 100 | 94.0 |
| 3 | 3 | 100 | 95.0 |
| 4 | 4 | 100 | 95.1 |
| 5 | 5 | 100 | 94.0 |
| 6 | 6 | 100 | 94.5 |
| 7 | 7 | 100 | 95.2 |
| 8 | 8 | 100 | 94.8 |
| 9 | 9 | 100 | 95.0 |
| 10 | 10 | 100 | 95.0 |

EXAMPLE 54

A copper halogeno complex, Li[CuCl$_3$].2H$_2$O, lithium chloride, and water were placed in a 1-liter four-necked flask to prepare a catalyst solution. After replacement of the atmosphere in the flask with oxygen, the catalyst solution was heated from the outside and vigorously stirred at 950 revolutions per minute (rpm). When the inner temperature reached 60° C., a 30% hexanol solution of 2,3,6-TMP was added dropwise at a rate of 38.3 grams per hour (g/hr) using a constant volume pump. 100% Oxygen was successively supplied from a gas holder, and the amount of oxygen consumed was measured with a wet-type gas flow meter. After 115 g of the 30% hexanol solution of TMP (0.25 mole of TMP) was added (the time required: 3 hours), its introduction was stopped. Subsequently, the resulting mixture was stirred for 1 hour at the same temperature. In this example, about 5 minutes of an induction period was observed. After the reaction, an aqueous layer and an organic layer were separated from each other. After the separation of the layers, the alcohol layer was analyzed by gas chromatography. The results are shown in Table 15.

TABLE 15

| Run No. | TMP/Complex/LiCl (molar ratio) | Total Concentration of Complex and LiCl (wt %) | Conversion of TMP (%) | Yield of TMBQ (%) | Yield of HMBP (%) | Yield of 4-Cl-TMP (%) |
|---|---|---|---|---|---|---|
| Example 54 | 1/0.25/0.75 | 41 | 100 | 96.2 | 2.3 | 0 |

EXAMPLES 55 TO 59

The procedure of Example 54 was repeated using 20 g of hexanol, but 0.2 g of cupric chloride, 0.3 g of cuprous chloride, or a mixture thereof were previously added to the catalyst solution. The induction period observed at the initial stage of the reaction in Example 54 was not observed in these examples. The results are shown in Table 16.

EXAMPLES 55 to 59

The procedure of Example 54 was repeated using 20 g of hexanol, but 0.2 g of cupric chloride, 0.3 g of cuprous chloride, or a mixture thereof were previously added to the catalyst solution. The induction period observed at the initial stage of the reaction in Example 54 was not observed in these examples. The results are shown in Table 16.

TABLE 16

| Run No. | Compound added previously | Conversion of TMP (%) | Yield of TMBQ (%) | Yield of HMBP (%) |
|---|---|---|---|---|
| Example 55 | Hexanol | 100 | 97.2 | 1.8 |
| Example 56 | Cupric hydroxide | 100 | 97.6 | 1.1 |
| Example 57 | Cuprous chloride | 100 | 97.3 | 1.1 |
| Example 58 | Hexanol + Cupric hydroxide | 100 | 97.5 | 1.2 |
| Example 59 | Hexanol + Cuprous chloride | 100 | 97.4 | 1.1 |

EXAMPLES 60 TO 69

The reaction was carried out using a gas having an oxygen concentration of 20% (air) and a gas having an oxygen concentration of 40% (air+100% oxygen) in the same manner as in Examples 55 to 59 except that the dropping rate of the TMP solution was 19.2 g/hr (the dropping period of time was 6 hours) in Example 68 and 28.75 g/hr (the dropping period of time was 4 hours) in the other examples. After the dropwise addition of the TMP solution was completed, the reaction mixture was stirred for 1.5 hours, and the products were analyzed. The results are shown in Table 17.

TABLE 17

| Run No. | Oxygen Concentration (%) | Compound added previously | Induction Period (min) | Conversion of TMP (%) | Yield of TMBQ (%) | Yield of HMBP (%) | Yield of 4-Cl-TMP (%) |
|---|---|---|---|---|---|---|---|
| Example 68 | 20 | — | 30 | 100 | 90 | 6.5 | 2.0 |
| Example 60 | 20 | Hexanol | 5 | 100 | 95 | 3.5 | 0.5 |
| Example 61 | 20 | Cupric hydroxide | 5 | 100 | 94.5 | 3.5 | 0.3 |
| Example 62 | 20 | Cuprous chloride | 5 | 100 | 94.7 | 3.0 | 0.6 |
| Example 63 | 20 | Hexanol + Cupric hydroxide | 0 | 100 | 96.8 | 2.1 | 0 |
| Example 69 | 40 | — | 10 | 100 | 91.5 | 6.5 | 0 |
| Example 64 | 40 | Hexanol | 0 | 100 | 97.2 | 1.9 | 0 |
| Example 65 | 40 | Cupric hydroxide | 0 | 100 | 97.4 | 1.0 | 0 |
| Example 66 | 40 | Cuprous chloride | 0 | 100 | 97.0 | 1.0 | 0 |
| Example 67 | 40 | Hexanol + Cupric hydroxide | 0 | 100 | 97.1 | 1.3 | 0 |

EXAMPLES 70 AND 71

The procedure of Example 55 was repeated but the dropping rate of the TMP solution was changed to 57.5 g/hr and 23 g/hr (the dropping period of time was 2 hours and 5 hours). The results are shown in Table 18.

TABLE 18

| Run No. | Dropping Period of Time (hr) | Conversion of TMP (%) | Yield of TMBQ (%) | Yield of HMBP (%) | Yield of 4-Cl—TMP (%) |
|---|---|---|---|---|---|
| Example 70 | 2.0 | 100 | 95.8 | 3.0 | 0.6 |
| Example 71 | 5.0 | 100 | 96.9 | 0.5 | 0 |

EXAMPLES 72 TO 76

The procedure of Example 55 was repeated using the alcohols described in Table 19 as the reaction solvent. The results are shown in Table 19.

TABLE 19

| Run No. | Alcohol | Conversion of TMP (%) | Yield of TMBQ (%) | Yield of HMBP (%) | Yield of 4-Cl—TMP (%) |
|---|---|---|---|---|---|
| Example 72 | n-Amyl alcohol | 100 | 97.1 | 2.0 | 0 |
| Example 73 | n-Heptyl alcohol | 100 | 97.0 | 1.8 | 0 |
| Example 74 | n-Octyl alcohol | 100 | 97.3 | 2.3 | 0 |
| Example 75 | n-Nonyl alcohol | 100 | 97.2 | 2.0 | 0 |
| Example 76 | n-Decyl alcohol | 100 | 97.0 | 2.0 | 0 |

EXAMPLES 77 AND 78

The procedure of Example 55 was repeated but the amount of the catalyst used was changed. The results are shown in Table 20.

TABLE 20

| Run No. | TMP/Complex/LiCl (molar ratio)* | Conversion of TMP (%) | Yield of TMBQ (%) | Yield of HMBP (%) | Yield of 4-Cl—TMP (%) |
|---|---|---|---|---|---|
| Example 77 | 1/1/3 | 100 | 95.0 | 2.1 | 1.1 |
| Example 78 | 1/0.5/1.5 | 100 | 96.3 | 2.0 | 0.8 |

Note:
*Catalyst concentration in the aqueous layer; 41 wt %.

EXAMPLE 79

The procedure of Example 55 was repeated but the catalyst concentration was increased. The results are shown in Table 21.

TABLE 21

| Run No. | Catalyst Concentration (%) | Conversion of TMP (%) | Yield of TMBQ (%) | Yield of HMBP (%) | Yield of 4-Cl—TMP (%) |
|---|---|---|---|---|---|
| Example 79 | 55 | 100 | 96.2 | 1.8 | 1.1 |

EXAMPLES 80 and 81

The procedure of Example 55 was repeated but the amount of lithium chloride added was changed, and the catalyst concentration was adjusted to 41%. The results are shown in Table 22.

TABLE 22

| Run No. | Amount of LiCl added (g) | TMP/Complex/LiCl (molar ratio) | Conversion of TMP (%) | Yield of TMBQ (%) | Yield of HMBP (%) | Yield of 4-Cl—TMP (%) |
|---|---|---|---|---|---|---|
| Example 80 | 16.6 | 1/0.25/2 | 100 | 94.1 | 2.0 | 3.0 |

TABLE 22-continued

| Run No. | Amount of LiCl added (g) | TMP/Complex/ LiCl (molar ratio) | Conversion of TMP (%) | Yield of TMBQ (%) | Yield of HMBP (%) | Yield of 4-Cl—TMP (%) |
|---|---|---|---|---|---|---|
| Example 81 | 4.2 | 1/0.25/0.5 | 100 | 93.5 | 5.0 | 0.8 |

EXAMPLE 82

In this example, the reaction was carried out batchwise.

Given amounts of a copper halogeno complex, Li[CuCl$_3$].2H$_2$O, lithium chloride, and water were placed in a 1-liter four-necked flask to prepare a catalyst solution. Then, 115 g of a 30% hexanol solution of 2,3,6-TMP was added to the flask and, after replacement of the atmosphere in the flask with oxygen, the resulting mixture was heated from the outside. When the inner temperature reached 60° C., the mixture was vigorously stirred at 950 rpm. Oxygen was successively supplied from a gas holder, and the amount of oxygen consumed was measured by the use of a wet-type gas flow meter. After gas absorption stopped, stirring was further continued for 1 hours at the same temperature. When the reaction was completed, the reaction mixture was separated into aqueous and alcohol layers. The alcohol layer was separated from the aqueous layer and analyzed by gas chromatography. The results are shown in Table 23.

TABLE 23

| Run No. | TMP/Complex/ LiCl (molar ratio) | Conversion of TMP (%) | Yield of TMBQ (%) | Yield of HMBP (%) | Yield of 4-Cl—TMP (%) |
|---|---|---|---|---|---|
| Example 82 | 1/0.25/0.75 | 100 | 87.5 | 11.0 | 0.2 |

EXAMPLES 83 AND 84

The procedure of Example 82 was repeated but the reaction was conducted in the presence of cuprous chloride or cupric hydroxide. The results are shown in Table 24.

TABLE 24

| Run No. | Compound added previously | Conversion of TMP (%) | Yield of TMBQ (%) | Yield of HMBP (%) | Yield of 4-Cl—TMP (%) |
|---|---|---|---|---|---|
| Example 83 | Cupric hydroxide 0.2 g | 100 | 86.7 | 10.8 | 0 |
| Example 84 | Cuprous chloride 0.15 g | 100 | 87.3 | 11.3 | 0 |

EXAMPLES 85 AND 86

The procedure of Example 83 was repeated but a gas having an oxygen concentration of 20% or 40% was used. The results are shown in Table 25.

TABLE 25

| Run No. | Oxygen Concentration (%) | Conversion of TMP (%) | Yield of TMBQ (%) | Yield of HMBP (%) | Yield of 4-Cl—TMP (%) |
|---|---|---|---|---|---|
| Example 85 | 20 | 100 | 85.1 | 12.3 | 0.5 |
| Example 86 | 40 | 100 | 86.0 | 11.0 | 0 |

EXAMPLES 87 AND 88

In Example 87, the procedure of Example 55 was repeated using Li$_2$[CuBr$_4$].6H$_2$O was used as the copper halogeno complex, and LiCl as the alkali metal halide.

In Example 88, the procedure of Example 82 was repeated using Li$_2$[CuBr$_4$].6H$_2$O as the copper halogeno complex, and LiCl as the alkali metal halide. The results are shown in Table 26.

TABLE 26

| Run No. | TMP/Complex/ LiCl (molar ratio) | Conversion of TMP (%) | Yield of TMBQ (%) | Yield of HMBP (%) | Yield of 4-Cl—TMP (%) |
|---|---|---|---|---|---|
| Example 87 | 1/0.3/1 | 100 | 90.1 | 6.5 | 0 |
| Example 88 | 1/4/1 | 100 | 87.9 | 10.1 | 0 |

EXAMPLES 89 TO 94

The procedure of Example 55 was repeated using the copper halogeno complexes and alkali metal halides shown in Table 27 were used. The results are set out in Table 27.

TABLE 27

| Run No. | Complex* | Alkali metal halide | Conversion of TMP (%) | Yield of TMBQ (%) | Yield of HMBP (%) | Yield of 4-Cl—TMP (%) |
|---|---|---|---|---|---|---|
| Example 89 | A | LiCl | 100 | 96.9 | 1.9 | 0 |
| Example 90 | B | " | 100 | 97.0 | 2.0 | 0 |
| Example 91 | C | " | 100 | 97.1 | 2.1 | 0 |
| Example 92 | D | " | 100 | 97.0 | 1.8 | 0 |
| Example 93 | E | CsCl | 100 | 96.9 | 2.3 | 0 |

TABLE 27-continued

| Run No. | Complex* | Alkali metal halide | Conversion of TMP (%) | Yield of TMBQ (%) | Yield of HMBP (%) | Yield of 4-Cl—TMP (%) |
|---|---|---|---|---|---|---|
| Example 94 | F | " | 100 | 96.8 | 2.4 | 0 |

Note:
*Complex A; (NH$_4$)[CuCl$_3$].2H$_2$O
*Complex B; K[CuCl$_3$].2H$_2$O
*Complex C; K$_2$[CuCl$_4$].2H$_2$O
*Complex D; Cs[CuCl$_3$]
*Complex E; Cs$_2$[CuCl$_4$].2H$_2$O
*Complex F; Cs$_2$[CuBr$_4$]

What is claimed is:

1. A process for producing 2,3,5-trimethylbenzoquinone which comprises contacting 2,3,6-trimethylphenol with molecular oxygen in a medium of water and an aliphatic alcohol having from 5 to 10 carbon atoms, the weight ratio of the water to the aliphatic alcohol being from 0.05 to 100 and the pH of the aqueous phase in the medium being 2.5 or less, in the presence of a copper halogeno complex catalyst represented by the general formula:

M$_l$(Cu(II)$_m$X$_n$)$_p$ wherein M is an alkali metal or ammonium, Cu(II) is a divalent copper, X is a halogen atom l is an integer of from 1 to 3, m is 1 or 2, n is an integer of from 3 to 8, p is 1 or 2, and 1+2mp=np, the concentration of the copper halogeno complex in the aqueous phase being from 20 to 80% by weight.

2. The process as claimed in claim 1, wherein the copper halogeno complex is Li[CuCl$_3$].2H$_2$O, NH$_4$[CuCl$_3$].2H$_2$(NH$_4$)$_2$[CuCl$_4$].2H$_2$), K[CuCl$_3$], K$_2$[CuCl$_4$]2H$_2$O, Cs[CuCl$_3$].2H$_2$O, Cs$_2$[CuCl$_4$].2H$_2$O, Cs$_3$[Cu$_2$Cl$_7$].2H$_2$O, Li$_2$[CuBr$_4$].bH$_2$O, K[CuBr$_3$], (NH$_4$)$_2$[CuBr$_4$].2H$_2$O, Cs$_2$[CuBr$_4$], or Cs[CuBr$_3$].

3. The process as claimed in claim 2, wherein the copper halogeno complex is Li[CuCl$_3$].2H$_2$O or Li$_2$[CuBr$_4$].6H$_2$. *Cs[CuCl$_3$].2H$_2$O, 4. The process as claimed in claim 1, wherein the amount of the copper halogeno complex used is from 0.1 to 5 moles per mole of 2,3,6-trimethylphenol.

5. The process as claimed in claim 1, wherein concentration of TMP in the aliphatic alcohol is from 10 to 80% by weight.

6. The process as claimed in claim 1, wherein the reaction temperature is from 10° to 120° C.

7. The process as claimed in claim 1, wherein the oxygen partial pressure in the reaction system is from 0.05 to 50 kg/cm$^2$ (absolute pressure).

8. A process for producing 2,3,5-trimethylbenzoquinone which comprises contacting 2,3,6-trimethylphenol with molecular oxygen in a medium of water and an aliphatic alcohol having from 5 to 10 carbon atoms, the weight ratio of the water to the aliphatic alcohol being from 0.05 to 100 and the pH of the aqueous phase in the medium being 2.5 or less, in the presence of a mixture of a copper halogeno complex catalyst represented by the general formula:

M$_l$(Cu(II)$_m$X$_n$)$_p$ wherein M is an alkali metal or ammonium, Cu(II) is a divalent copper, X is a halogen atom, l is an integer of from 1 to 3, m is 1 or 2, n is an integer of from 3 to 8, p is 1 or 2, and 1+2mp=np, and an alkali metal halide, the concentration of the copper halogeno complex in the aqueous phase being from 20 to 80% by weight.

9. The process as claimed in claim 8, wherein the alkali metal halide is at least one selected from the group consisting of NaCl, LiCl, KCl, CsCl, NaBr, NH$_4$Br, KBr, CsBr, NaI, LiI, KI, and CsI.

10. The process as claimed in claim 9, wherein the alkali metal halide is LiCl.

11. The process as claimed in claim 8, wherein the molar ratio of alkali metal halide to copper halogeno complex is from 1 to 15.

12. The process as claimed in claim 8, wherein the copper halogeno complex is Li[CuCl$_3$].2H$_2$O, NH$_4$[CuCl$_3$].2H$_2$O, (NH$_4$)$_2$[CuCl$_4$].2H$_2$O, K[CuCl$_3$], K$_2$[CuCl$_4$].2H$_2$O, Cs$_2$[CuCl$_4$].2H$_2$O, Cs$_3$[Cu$_2$Cl$_7$].2H$_2$O, (NH$_4$)$_2$[CuBr$_4$].2H$_2$O, Cs$_2$[CuBr$_4$], or Cs[CuBr$_3$]O.

13. The process as claimed in claim 12, wherein the copper halogeno complex is Li[CuCl$_3$].2H$_2$O or Li$_2$[CuBr$_4$].6H$_2$O.

14. The process as claimed in claim 8, wherein the amount of a copper halogeno complex used is from 0.1 to 5 moles per mole of 2,3,6-trimethylphenol.

15. The process as claimed in claim 8, wherein concentration of TMP in the aliphatic alcohol is from 10 to 80% by weight. *Cs[CuCl$_3$].2H$_2$O, Li$_2$[CuBr$_4$].6H$_2$O, K[CuBr$_3$], 16. The process as claimed in claim 8, wherein the concentration of the mixture of the copper complex and alkali metal halide in the aqueous phase of the reaction system is from 20 to 80% by weight.

17. A process for preparing 2,3,5-trimethylbenzoquinone contacting 2,3,6-trimethylphenol with oxygen or oxygen-containing gas having an oxygen concentration of at least 205% in an aqueous solution of a catalyst comprising a copper halogeno complex represented by the general formula (I) and an alkali metal halide, M$_l$[Cu(II)$_m$X$_n$]$_p$ wherein M is an alkali metal or ammonium, Cu(II) is divalent copper, X is halogen, l is an integer of 1 to 3, m is 1 or 2, n is an integer of 3 to 8, p is 1 or 2, and 1+2mp=np; said contact reaction of 2,3,6-trimethylphenol with the oxygen or the oxygen-containing gas being carried out semi-batchwise while continuously adding a solution of 2,3,6-trimethylphenol in an aliphatic alcohol having from 5 to 10 carbon atoms to the aqueous solution of the catalyst to which an aliphatic alcohol having from 5 to 10 carbon atoms, cupric hydroxide, cuprous chloride or a mixture thereof has previously been allowed.

18. The process as claimed in claim 17, wherein the solution of 2,3,6-trimethylphenol is added over a period of at least 2 hours.

19. The process as claimed in claim 17, wherein the aliphatic alcohol having from 5 to 10 carbon atoms is selected from the group consisting of n-amyl alcohol, n-hexyl alcohol, 2-ethyl hexanol, n-heptyl alcohol, n-octyl alcohol, n-nonyl alcohol, and n-decyl alcohol.

20. The process as claimed in claim 17, wherein the concentration of 2,3,6-trimethylphenol in the aliphatic alcohol having from 5 to 10 carbon atoms is from 5 to 50 percent by weight.

21. The process as claimed in claim 17, wherein the weight ratio of the amount of the aliphatic alcohol having from 5 to 10 carbon atoms as previously added to the aqueous solution of the catalyst to the total amount of the alcohol being added is from 0.05:1 to 1.3:1.

22. The process as claimed in claim 17, wherein the amount of the cupric hydroxide previously added to the aqueous solution of the catalyst is from 0.01 to 0.05 mole per mole of the copper halogeno complex used.

23. The process as claimed in claim 17, wherein the amount of cuprous chloride previously added to the aqueous solution of the catalyst is from 0.01 to 0.05 mole per mole of the copper halogeno complex used.

24. The process as claimed in claim 17, wherein the copper halogeno complex is selected from the group consisting of $Li[CuCl_3].2H_2O$, $NH_4[CuCl_3].2H_2O$, $(NH_4)_2[CuCl_4].2H_2O$, $K_2[CuCl_4].2H_2O$, $Cs[CuCl_3].2H_2O$, $Cs_2[CuCl_2[CuCl_4].2H_2O$, $Li_2[CuBr_4].6H_2O$, $K[CuBr_3]$, $(NH_4)_2[CuBr_4].2H_2O$, *** $Cs[CuBr_3]$.

25. The process as claimed in claim 17, wherein the alkali metal halide is at least one selected from the group consisting of NaCl, LiCl, KCl, CsCl, NaBr, $NH_4Br$, KBr, CsBr, NaI, LiI, KI, and CsI.

26. The process as claimed in claim 17, wherein the molar ratio of the copper halogeno complex to the alkali metal halide is from 1:1 to 1:15.

27. The process as claimed in claim 17, wherein the total concentration of the copper halogeno complex and alkali metal halide in the aqueous layer of the reaction system is from 20 to 80 percent by weight.

28. The process as claimed in claim 17, wherein the oxygen concentration of the gas used is essentially 100 percent.

29. The process as claimed in claim 17, wherein air is used as the oxygen-containing gas. $K[CuCl_3]$, $Cs_3[Cu_2Cl_7].2H_2O$, $Cs_2[CuBr_4]$, and 30. A process for producing 2,3,5-trimethylbenzoquinone which comprises contacting 2,3,6-trimethylphenol with molecular oxygen in a medium of water and an aliphatic alcohol having from 5 to 10 carbon atoms, in the presence of a copper halogeno complex catalyst represented by the general formula:

$$M_l[Cu(II)_m X_n]_p$$

wherein m is an alkali metal or ammonium, Cu(II) is divalent copper, X is halogen, l is an integer of from 1 to 3, m is 1 or 2, n is an integer of from 3 to 8, p is 1 or 2, and $l+2$ mp=np, a mixture of a copper halogeno complex as just defined and an alkali metal halide or a mixture of a copper halogeno complex as just defined, an alkali metal and cupric hydroxide and/or cuprous chloride.

* * * * *

UNITED STATES PATENT AND TRADEMARK OFFICE
CERTIFICATE OF CORRECTION

PATENT NO. : 4,828,762

DATED : May 9, 1989

INVENTOR(S) : ISSHIKI et al

It is certified that error appears in the above-identified patent and that said Letters Patent is hereby corrected as shown below:

Title Page, ABSTRACT, lines 6, 8 and 9, after "copper" delete "halogen" and replace with --halogeno--.

line 15, after "integer" delete --or--.
and repace with --of--.

Column 25, line 32, (Claim 2), after "complex is" delete remainder of claim and replace with the following:

--$Li[CuCl_3] \cdot 2H_2O$, $NH_4[CuCl_3] \cdot 2H_2O$, $(NH_4)_2[CuCl_4] \cdot 2H_2O$, $K[CuCl_3]$, $K_2[CuCl_4] \cdot 2H_2O$, $Cs[CuCl_3] \cdot 2H_2O$, $Cs_2[CuCl_4] \cdot 2H_2O$, $Cs_3[Cu_2Cl_7] \cdot 2H_2O$, $Li_2[CuBr_4] \cdot 6H_2O$, $K[CuBr_3]$, $(NH_4)_2[CuBr_4] \cdot 2H_2O$, $Cs_2[CuBr_4]$, or $Cs[CuBr_3]$.--

Column 25, line 38 (Claim 3), after "complex is" delete remainder of claim and replace with the following:

--$Li[CuCl_3] \cdot 2H_2O$ or $Li_2[CuBr_4] \cdot 6H_2O$.--

UNITED STATES PATENT AND TRADEMARK OFFICE
CERTIFICATE OF CORRECTION

PATENT NO. : 4,828,762

DATED : May 9, 1989

INVENTOR(S) : ISSHIKI et al

It is certified that error appears in the above-identified patent and that said Letters Patent is hereby corrected as shown below:

Column 26, line 23, (Claim 12), after "complex is" delete remainder of claim and replace with the following:

--$Li[CuCl_3] \cdot 2H_2O$, $NH_4[CuCl_3] \cdot 2H_2O$, $(NH_4)_2[CuCl_4] \cdot 2H_2O$, $K[CuCl_3]$, $K_2[CuCl_4] \cdot 2H_2O$, $Cs[CuCl_3] \cdot 2H_2O$, $Cs_2[CuCl_4] \cdot 2H_2O$, $Cs_3[Cu_2Cl_7] \cdot 2H_2O$, $Li_2[CuBr_4] \cdot 6H_2O$, $K[CuBr_3]$, $(NH_4)_2[CuBr_4] \cdot 2H_2O$, $Cs_2[CuBr_4]$, or $Cs[CuBr_3]$.--.

Column 26, line 36, (Claim 15), after "weight.", delete remainder of claim.

Column 26, line 43, (Claim 17), before "contacting" insert --by--;
 line 45, after "at least" delete "205%" and replace with --20%--.

Column 27, line 23, (Claim 24), after "consisting of" delete remainder of claim and replace with the following:

--$Li[CuCl_3] \cdot 2H_2O$, $NH_4[CuCl_3] \cdot 2H_2O$, $(NH_4)_2[CuCl_4] \cdot 2H_2O$, $K[CuCl_3]$, $K_2[CuCl_4] \cdot 2H_2O$, $Cs[CuCl_3] \cdot 2H_2O$, $Cs_2[CuCl_4] \cdot 2H_2O$, $Cs_3[Cu_2Cl_7] \cdot 2H_2O$, $Li_2[CuBr_4] \cdot 6H_2O$, $K[CuBr_3]$, $(NH_4)_2[CuBr_4] \cdot 2H_2O$, $Cs_2[CuBr_4]$, or $Cs[CuBr_3]$.--.

UNITED STATES PATENT AND TRADEMARK OFFICE
CERTIFICATE OF CORRECTION

PATENT NO. : 4,828,762

DATED : May 9, 1989

INVENTOR(S) : ISSHIKI et al

It is certified that error appears in the above-identified patent and that said Letters Patent is hereby corrected as shown below:

Column 28, line 12 (claim 29), after "gas." delete remainder of claim.

Signed and Sealed this

Fifth Day of January, 1993

Attest:

DOUGLAS B. COMER

Attesting Officer

Acting Commissioner of Patents and Trademarks